United States Patent [19]

Brocks et al.

[11] Patent Number: 5,679,583

[45] Date of Patent: Oct. 21, 1997

[54] MONOCLONAL ANTIBODIES FOR THE SELECTIVE IMMUNOLOGICAL DETERMINATION OF INTACT PROCOLLAGEN PEPTIDE (TYPE III) AND PROCOLLAGEN (TYPE III) IN BODY FLUIDS

[75] Inventors: Dietrich Brocks, Wiesbaden; Jürgen Pünter, Hofheim am Taunus; Helmut Strecker, deceased, late of Pfungstadt, by Renate Strecker, heir; Rupert Timpl, Gauting; Volkmar Günzler-Pukall, Marburg; Henning Hachmann, Frankfurt am Main, all of Germany

[73] Assignee: Hoechst Aktiengesellschaft, Frankfurt am Main, Germany

[21] Appl. No.: 417,197

[22] Filed: Apr. 5, 1995

Related U.S. Application Data

[63] Continuation of Ser. No. 2,796, Jan. 11, 1993, abandoned, which is a continuation-in-part of Ser. No. 800,717, Dec. 3, 1993, abandoned, which is a continuation of Ser. No. 189,059, May 2, 1988, abandoned, and a continuation-in-part of Ser. No. 863,532, Apr. 6, 1992, abandoned, which is a continuation of Ser. No. 342,781, Apr. 25, 1989, abandoned, and a continuation-in-part of Ser. No. 863,875, Apr. 6, 1992, abandoned, which is a division of Ser. No. 342,781, Apr. 25, 1989, abandoned.

[30] Foreign Application Priority Data

May 2, 1987 [DE] Germany ............... 37 14 633.5
Apr. 27, 1988 [DE] Germany ............... 38 14 216.3

[51] Int. Cl.[6] .............. G01N 33/543; G01N 33/53; C12N 5/20; C07K 16/18
[52] U.S. Cl. .............. 436/518; 435/332; 436/548; 530/388.2
[58] Field of Search .................. 436/518, 548; 435/7.94, 332; 530/388.2

[56] References Cited

U.S. PATENT DOCUMENTS

| | | | |
|---|---|---|---|
| 4,312,853 | 1/1982 | Timpl et al. | 436/540 |
| 4,504,587 | 3/1985 | Timpl et al. | 435/7.23 |
| 4,628,027 | 12/1986 | Gay | 436/528 |
| 4,722,903 | 2/1988 | Kudryk et al. | 435/7.4 |

FOREIGN PATENT DOCUMENTS

| | | |
|---|---|---|
| 0 004 940 | 10/1979 | European Pat. Off. . |
| 0 089 008 | 9/1983 | European Pat. Off. . |
| 0 289 930 | 11/1988 | European Pat. Off. . |

OTHER PUBLICATIONS

Sevier et al., Monoclonal Antibodies in Clinical Immunology, Clin. Chem. 27:1797–1806, 1981.

Rohde, H., et al., "Radioimmunoassay For Type III Procollagen Peptide And Its Application To Human Liver Disease," Eur. J. Clin. Invest., 9: 451–459 (1979).

Niemela, O., et al., "Heterogeneity Of The Antigens Related To The Amino-terminal Propeptide Of Type III Procollagen in Human Serum," Clinica Chimica Acta, 124: 39–44 (1982).

SundarRaj, N., et al., "Development And Characterization of Monoclonal Antibodies To Human Type III Procollagen," Biochem. And Biophys. Res. Comm., 106(1)48–57 (1982).

SundarRaj, N. et al., Chemical Abstracts, 97: 4431s (1982).

Niemela, O., et al., "Radioimmunoassays For Type III Procollagen Amino-Terminal Peptides In Humans," Clin. Chem., 31(8): 1301–1304 (1985).

Kondo, H., "Establishment Of Mouse Monoclonal Antibodies Against Amino Terminal Peptide Of Type III Procollagen And Their Use For A Histochemical Study In The Human Liver," Jpn. J. Gastroenterol., 83: 2174–2180 (1986).

Kondo, H., Biological Abstracts, 83(6): 52561 (1987).

Brocks, D., et al., Chemical Abstracts, 111(19): 170640m (1989).

*Primary Examiner*—Marian C. Knode
*Assistant Examiner*—Donna C. Wortman
*Attorney, Agent, or Firm*—Finnegan, Henderson, Farabow, Garrett & Dunner, L.L.P.

[57] ABSTRACT

It is possible with the aid of a monoclonal antibody which is specifically directed against an epitope of amino-terminal procollagen peptide (type III) which is not present on the fragment Col 1, and of a second monoclonal or polyclonal antibody against an epitope of amino-terminal procollagen peptide (type III), to determine said peptide with great accuracy. It is also, possible, with the aid of a monoclonal antibody which is specifically directed against an epitope of amino-terminal procollagen peptide (type III) which is not present in Col 1, to determine with great accuracy said procollagen peptide in body fluids.

25 Claims, 6 Drawing Sheets

MONOCLONAL ANTIBODIES FOR THE SELECTIVE IMMUNOLOGICAL DETERMINATION OF INTACT PROCOLLAGEN PEPTIDE (TYPE III) AND PROCOLLAGEN (TYPE III) IN BODY FLUIDS

This application is a continuation of U.S. patent application Ser. No. 08/002,796, filed Jan. 11, 1993, abandoned, which is a continuation-in-part of U.S. patent application Ser. No. 07/800,717, filed Dec. 3, 1991, abandoned, which is a continuation of U.S. patent application Ser. No. 07/189,059, filed May 2, 1988, now abandoned; and a continuation-in-part of U.S. patent application Ser. No. 07/863,532, filed Apr. 6, 1992, abandoned, which is a continuation of U.S. patent application Ser. No. 07/342,781, filed Apr. 25, 1989, now abandoned; and a continuation-in-part of U.S. patent application Ser. No. 07/863,875, filed Apr. 6, 1992, abandoned, which is a divisional of U.S. patent application Ser. No. 07/342,781, filed Apr. 25, 1989, abandoned. All of these U.S. patent applications are hereby specifically incorporated by reference herein.

BACKGROUND AND SUMMARY OF THE INVENTION

Procollagen peptide (type III) (P III P) is the amino-terminal propeptide of collagen (type III) which is cleaved off outside the cell after secretion of the procollagen (type III molecule. Procollagen peptide (type III) in turn can be further cleaved with collagenase to fragments Col 1, Col 2 and Col 3, which can be isolated using methods of protein chemistry known per se (Nowack, H. et al., Euro. J. Biochem. 70, 205–216 (1976); Bruckner, P. et al., Eur. J. Biochem. 90, 595–603 (1978)).

The concentration of this procollagen peptide in body fluids can be determined using a radioimmunological determination method as described in European Patent No. 4940. Knowledge of the serum concentration of the peptide allows conclusions to be drawn about the activity of fibrotic disorders, such as, for example, of the liver (Rohde, H. et al., Euro. J. Clin. Invest. 9, 451–459 (1979)).

However, accurate selective determination of procollagen peptide (type III) in serum and other body fluids is not possible using the methods hitherto described, because the polyclonal antibodies which are used in these methods react, with different, lower affinity, with various antigens which occur in serum and some of which are breakdown products of procollagen peptide (type III) (Niemela, O. et al., Clin. Chim. Acta 124, 39–44 (1982)). The result of this is that the serum dilution plots and the dilution plots of other body fluids are not parallel to the calibration plot constructed using pure procollagen peptide (type III), and hence it is necessary to determine the antigen content in several dilutions of each unknown sample in order to establish the antigen concentration via the 50% intercept on the dilution plot.

This technical problem can be solved using the method of European Patent Application 0,089,008, in which the antibodies used have comparable affinities for intact procollagen peptide (type III) and its breakdown product Col 1. This method determines intact and degraded procollagen peptide (type III) together, but this results in imprecision in the diagnostic conclusions because the normal population and the patient population may overlap greatly.

An accurate selective determination of procollagen peptide (type III) and procollagen (type III) in serum and other body fluids has also been proposed in European Patent Application 289,930. However, this entails the necessity for a number of centrifugation steps which make routine laboratory use of this test difficult. More straightforward manipulation is permitted by the immunoradiometric assay (IRMA) method. This method makes use of two antibodies one of which is coupled to a solid carrier, which makes one precipitation step and thus one centrifugation and some pipetting steps redundant.

Surprisingly, a monoclonal antibody which does not react with the breakdown products of procollagen peptide (type III) which occur in body fluids has now been found. Use of this monoclonal antibody makes possible an immunological determination of the amino-terminal procollagen peptide (type III), which does not also determine its breakdown products and which is distinguished by serum dilution curves, the dilution curves of other body fluids and the calibration curve showing complete parallelism.

A different monoclonal antibody which reacts with a fragment of procollagen (type III) which has not hitherto been evident as a characteristic peak in the gel filtration chromatography has also, surprisingly, been found. This antibody, in combination with other monoclonal polyclonal antibodies with specificity for procollagen peptide (type III) and/or procollagen (type III), permits the determination of these antigens using the IRMA technique.

Hence the invention relates to:

1. A monoclonal antibody having the reaction pattern which is depicted in FIG. 3 towards intact procollagen (type III) and pN collagen (procollagen which is lacking the C-terminal propeptide, peak 4a), intact amino-terminal procollagen peptide (type III) (peak 5a), and Col 1 and breakdown products of the amino-terminal procollagen peptide (type III) having the same molecular weight as Col 1 (peak 6a).
2. A monoclonal antibody having the reaction pattern depicted in FIG. 5 towards intact procollagen (type III) and pN-collagen (procollagen lacking the C-terminal propeptide) (peak 1a), intact amino-terminal procollagen peptide (type III) (peak 2a) degradation products of amino-terminal procollagen peptide (type III) whose molecular weights are between that of amino-terminal procollagen peptide (type III) and that of Col 1 (peak 3a), as well as Col 1 and degradation products of amino-terminal procollagen peptide (type III) with the same molecular weight as Col 1 (peak 4a).
3. A hybridoma cell line which is formed by fusion of cells from a myeloma line and lymphocytes from an animal which has previously been immunized with procollagen peptide (type III), and which produces the antibodies described in 1 and 2.
4. A process for the preparation of the antibodies described under 1 or 2.
5. A method for the quantitative immunological determination of procollagen peptide (type III) using the antibodies described under 1 or 2.
6. A diagnostic composition for establishing the amount of procollagen peptide (type III) in body fluids, which is composed of an effective amount of the monoclonal antibodies described in 1 or 2, mixed with a diagnostically acceptable vehicle.
7. A diagnostic composition for establishing the amount of procollagen peptide (type III) in body fluids, which is composed of an effective amount of the monoclonal antibodies defined under 1 or 2, alone or in combination with other antibodies, in particular with an effective amount of the monoclonal antibody proposed in European Patent Application 289,930, mixed with a carrier acceptable in diagnosis.

The invention is explained in detail hereinafter, especially the preferred embodiments. The invention is also defined in the patent claims.

DESCRIPTION OF THE PREFERRED EMBODIMENTS

For the preparation of the monoclonal antibodies, it is possible for animals, preferably rabbits or rodents such as, for example, mice, rats, or guinea pigs, to be immunized, in the presence of adjuvant, with procollagen peptide (type III) which has been isolated by the process of European Patent 4940. Mice are particularly preferably used, especially those of the SJL strain. The immune response is enhanced with repeated booster injections, for example at intervals of 3 to 8 weeks. The success of the immunization is checked by determining the concentration of antibodies in a radioimmunological binding assay (R. Timpl and L. Risteli, Immunochemistry of the Extracellular Matrix, H. Furthmayr Ed. Vol. 1, 199 (1982)). Some days before the fusion of the lymphocytes with a myeloma cell line, the animals are treated with procollagen peptide (type III) without adjuvant. Lymphocytes are obtained from the animals and fused with a myeloma cell line which can likewise originate from one of the above-mentioned animal species, but is preferably from the mouse, in particular the cell line P3X63AG8.653. It is advantageous to fuse lymphocytes with myeloma cell lines of the same species. The fusion and the further cultivation of the cell clones are carried out in a manner known to those skilled in the art with the concentration of specific antibodies being determined in the supernatant from the cell cultures using an immunological binding assay. Clones suitable for use in immunological methods are selected from the cell clones derived from the fusion. It is particularly preferable to use a cell line which is prepared by fusion of lymphocytes from mice to the SJL strain immunized against procollagen peptide type III with the mouse myeloma cell line P3X63AG8.653. The latter cell line is deposited at the European Collection of Animal Cell Cultures (ECACC), PHLS Centre for Applied Microbiology and Research, Porton Down, Salisbury, SP4 0JG, U.K., under the number 87042308.

A clone is chosen for use in the IRMA from the cell clones derived from this process. It is particularly preferable to use a cell line which is prepared by fusion of the mouse myeloma cell line P3X63AG8.653 with lymphocytes from mice of the SJL strain which have been immunized with procollagen peptide (type III), and which produces monoclonal antibodies having the reaction pattern shown in FIG. 5. This cell line was deposited on Mar. 2, 1988, under the conditions of the Budapest Treaty at the European Collection of Animal Cell Cultures (ECACC) with the number 88030202.

Figure 3:
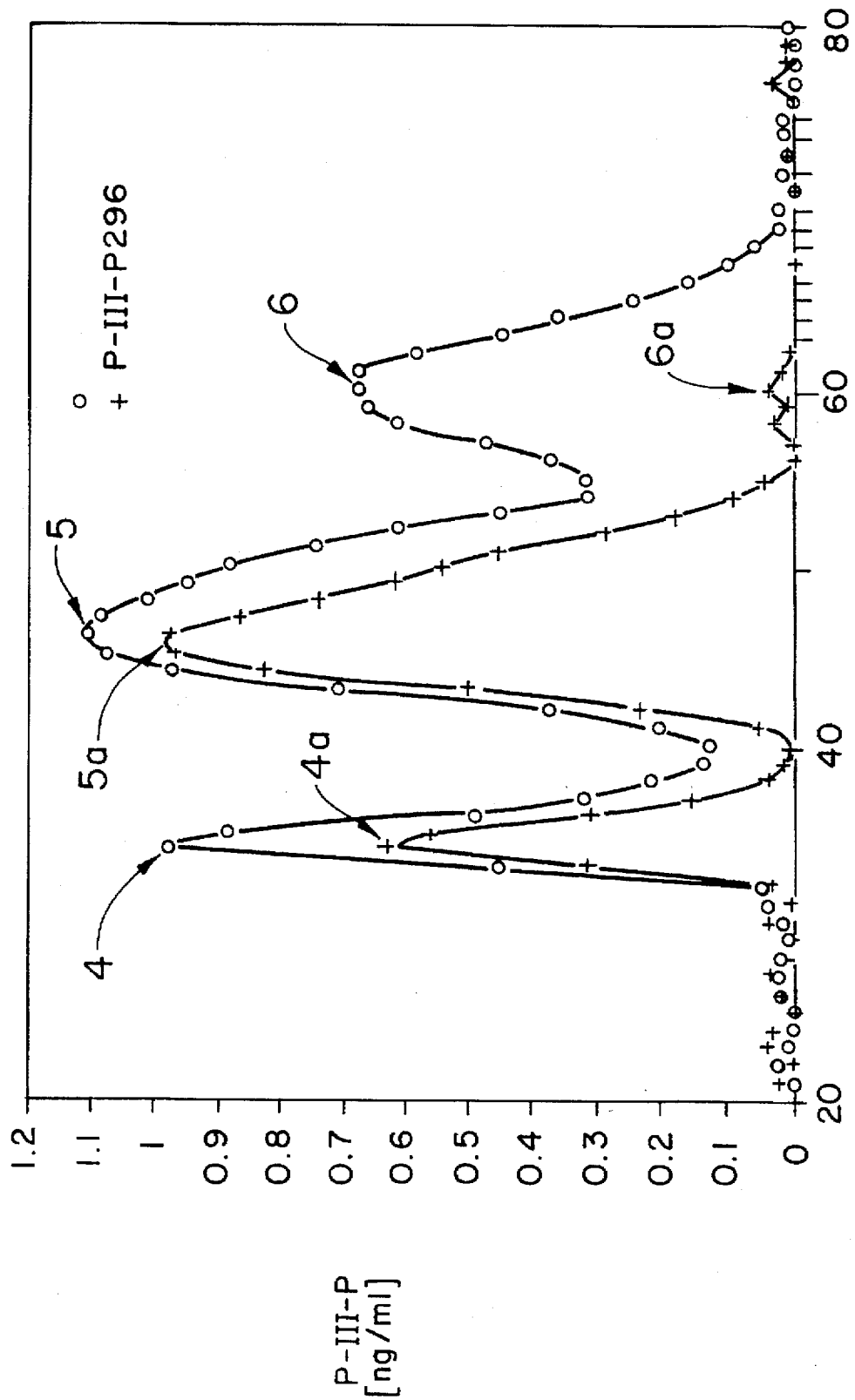
FIG. 3. The elution profile of the antigen determined using P III P 296 indicated by (+), comparing with the profile of the antigen determined using the polyclonal antibodies indicated by (o). Peak 4/4a corresponds to pN collagen and intact amino-terminal procollagen (type III). Peak 5/5a corresponds to amino-terminal procollagen peptide (type III) =(P III P). Peak 6/6a corresponds to Col 1 and breakdown products of amino-terminal procollagen peptide (type III) with the same molecular weight as Col 1.

The monoclonal antibodies according to the invention belong in the group of immunoglobulins, preferably in the class of IgG, IgA and IgM proteins. Antibodies of the IgG class, especially of the subclass IgG2b, can be used with particular advantage. The antibody according to the invention is particularly surprising because its affinity for the antigen is higher than the affinity of polyclonal antibodies. The opposite is normally found. The properties of the monoclonal antibodies are illustrated by the monoclonal antibody P III P 296, which is obtained from the cell line ECACC 87042308, if the antigens present in the serum are fractionated according to their molecular weight by gel filtration chromatography and the fractions from the chromatography are used in a radioimmunoassay. It emerges from this that the antigen fraction which is also detected on analysis with polyclonal antibodies and has the molecular weight of the breakdown product Col 1 is not detected by the monoclonal antibodies according to the invention. FIG. 3 shows the elution profile of the gel filtration chromatography of human serum as shown by the monoclonal antibody, comparing with the elution profile as shown by polyclonal antibodies. Peak 4/4a corresponds to intact procollagen type III and pN collagen type III (Rohde H. et al., Eur. J. Biochem. 135, 197 (1983)). Peak 5/5a corresponds to intact amino-terminal procollagen type III (P III P), whereas peak 6/6a corresponds to Col 1 together with breakdown products of amino-terminal procollagen peptide type III with the same molecular weight as Col 1 (Rohde H. et al., Eur. J. Biochem 135, 197 (1983)). The concentration of the substances in the relevant fractions can be determined with the aid of a procollagen peptide type III calibration plot.

Figure 5:
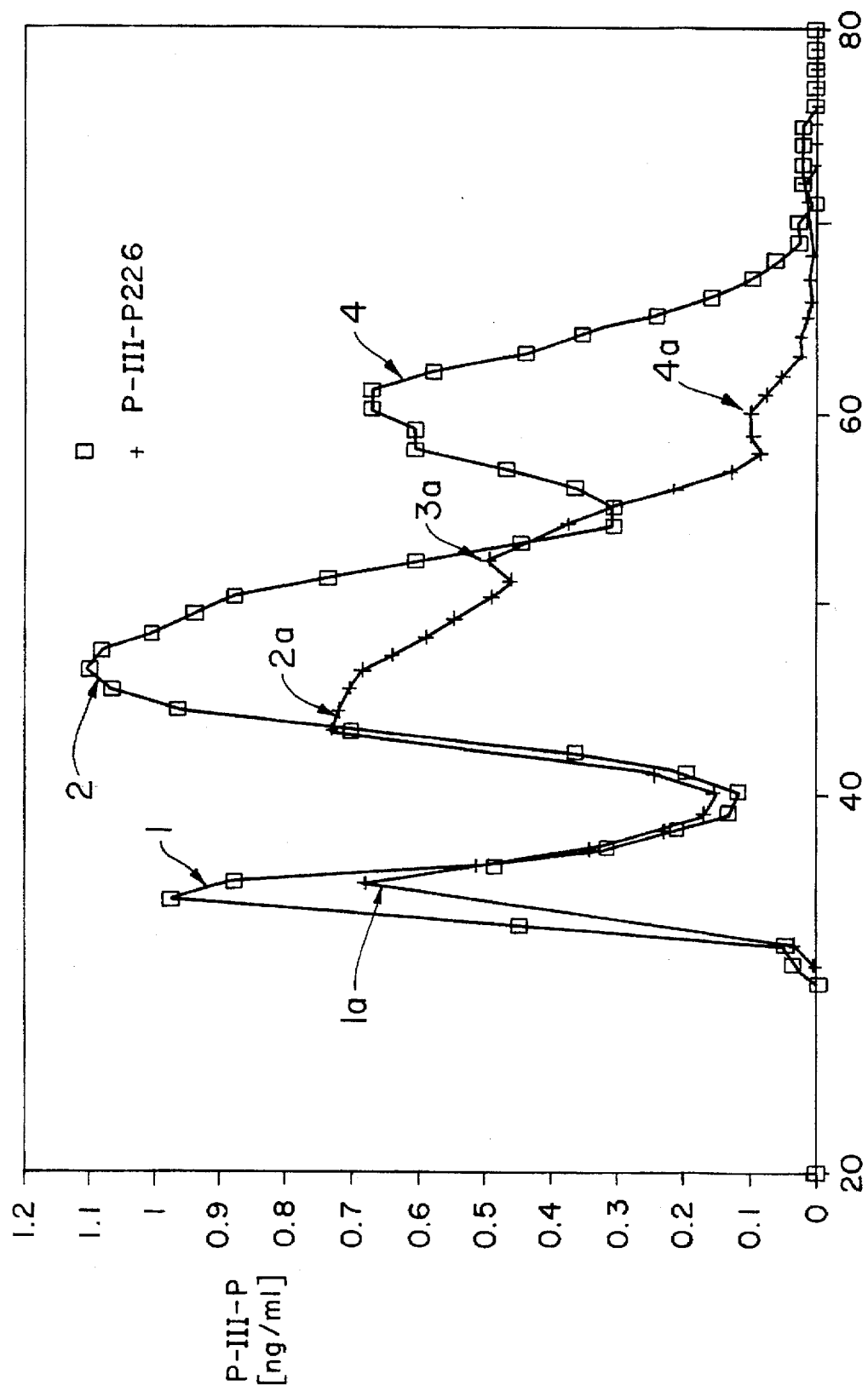
FIG. 5. The gel filtration chromatography elution profile as shown by the monoclonal antibody P III P 226 indicated by (+) compared with the elution profile exhibited by polyclonal antibodies indicated by ([ ]). Peak 1/1a corresponds to intact procollagen (type III) and pN-collagen (type III). Peak 2/2a corresponds to intact amino-terminal procollagen peptide (type III) and degradation products thereof with a similar size. Peak 3a covers degradation products of procollagen peptide (III) which produce in the chromatogram a peak with is smaller than that of procollagen peptide (type III) but larger than that of Col 1. The peak 4/4a corresponds to Col 1 plus degradation products of the amino-terminal procollagen peptide (type III) with the same molecular weight as Col. 1.

The properties of the monoclonal antibodies are also illustrated using the monoclonal antibody P III P 226 obtained from the cell line ECACC 88030202, when the antigens present in the serum are fractionated according to their molecular weight by gel filtration chromatography and the fractions from the chromatography are employed in the radioimmunoassay. FIG. 5 shows the gel filtration chromatography elution profile as shown by the monoclonal antibody P III P 226 compared with the elution profile exhibited by polyclonal antibodies. Peak 1/1a corresponds to intact procollagen (type III) and pN-collagen (type III). Peak 2/2a corresponds to intact amino-terminal procollagen peptide (type III) and degradation products thereof with a similar size. Peak 3a covers degradation products of procollagen peptide (III) which produce in the chromatogram a peak with is smaller than that of procollagen peptide (type III) but distinctly larger than that of Col 1. Thus the molecular weight of each of the degradation products is between about 45,000 (procollagen peptide) and about 10,000 (Col 1). The peak 4/4a corresponds to Col 1 plus degradation products of the amino-terminal procollagen peptide (type III) with the same molecular weight as Col 1. It emerges that the antigen fraction which is also detected on analysis with polyclonal antibodies and which has the molecular weight of the degradation product Col 1, or is Col 1 is detected distinctly more weakly by the monoclonal antibody according to the invention. The monoclonal antibody according to the invention thus has a specific action against an epitope of the amino-terminal procollagen peptide (type III) which is not present in Col 1. Furthermore, some of the antigens detected by polyclonal antibodies in peak 2 are not recognized by the antibody P III P 226, so that with the antibody P III P 226 two peaks (2a and 3a) are evident at the position of peak 2. Peak 3a is likewise not found using the antibody P III P 296 proposed in the German Patent Application.

It is important for the preparation of the antibodies according to the invention that a suitable source is available for obtaining the antigen. As already mentioned, highly purified human or animal procollagen peptide (type III) is advantageously isolated by the process of European Patent 4,940, entailing breakdown of tissue or pathological body fluids with collagenase, and removal of the procollagen peptide from the reaction solution and purification by combination of chromatographic methods and/or immunoadsorption.

The monoclonal antibody according to the invention can be used in a variety of immunological methods, including all types of radioimmunoassay, for example, sequential saturation analysis or equilibrium analysis, as well as in other competitive and noncompetitive binding assays, such as fluorescence, enzyme, chemiluminescence or other immunoassays. It is especially suitable for use in sandwich methods in immunosorbent assays. The monoclonal antibody can therefore be employed in immunological methods for the isolation and characterization, as well as for the quantitative determination, of procollagen peptide (type III) in tissues and body fluids. The methods used are those known per se to those skilled in the art, advantageously entailing reaction of a liquid sample which contains procollagen peptide (type III) with the monoclonal antibody according to the invention, which is coupled to a solid matrix which is preferably composed of plastic material, in particular plastic tubes, and determination of the amount of procollagen peptide (type III) by binding of a polyclonal or of a second monoclonal antibody, preferably of the monoclonal antibody proposed in European Patent Application 289,930, which is provided with a radioactive or other tracer. This method can also be carried out by binding polyclonal or monoclonal antibodies, especially the monoclonal antibody proposed in European Patent Application 289,930, to a solid matrix and bringing about reaction with the antigen, with this antigen then being determined quantitatively by binding of the labeled antibody according to the invention. In these methods it is immaterial whether the procollagen peptide (type III) is still linked to the amino terminus of procollagen (type III) or not. The degradation products of procollagen peptide (type III), especially Col 1, which have hitherto interfered with the immunological determination using polyclonal antibodies, are not detected by the assay system described.

The monoclonal antibody proposed in European Patent Application 289,930 exhibits the reaction pattern depicted in FIG. 3 towards intact procollagen (type III) and pN-collagen (procollagen lacking the C-terminal propeptide, peak 4a), intact amino-terminal procollagen peptide (type III) (peak 5a) as well as Col 1 and degradation products of amino-terminal procollagen peptide (type III) with the same molecular weight as Col 1 (peak 6a).

The procedure for the preparation of this monoclonal antibody is essentially that described above. It is particularly preferred to use a cell line prepared by fusion of the mouse myeloma cell line P3X63AG8.653 with lymphocytes from mice of the SJL strain immunized with procollagen peptide (type III). This cell line is deposited at the European Collection of Animal Cell Cultures (ECACC), PHLS Centre for Applied Microbiology and Research, Porton Down, Salisbury, SP4 OJG, U.K. under the number 87042308.

The monoclonal antibody according to the invention can also be used, where appropriate after labeling with chloramine T or Bolton-Hunter reagent (Felber, Meth. Biochem. Anal. 22, 1 (1974); Shelley et al., Clin. Chem. 19, 146 (1975)) and in other competitive and noncompetitive binding assays, such as fluorescence or enzyme immunoassays, chemiluminescence or other immunoassays, including immunoradiometric assay (IRMA). The monoclonal antibody can thus be used in immunological methods for the isolation and characterization and for the quantitative determination of procollagen peptide (type III) in tissues and body fluids. The methods used are known per se to the expert and entail reacting a liquid sample which contains procollagen peptide (type III) with the monoclonal antibody according to the invention, either in solution or on a solid carrier, and determination of the amount of procollagen peptide (type III) via the antigen/antibody complex formed. It is of no consequence for this whether the procollagen peptide (type III) is still linked to the amino terminus of procollagen (type III) or not. The breakdown products of procollagen peptide (type III), especially Col 1, which have hitherto interfered in the immunological determination, are not among the species detected by the antibody according to the invention.

The invention is explained further in the examples which follow. Unless otherwise indicated, percentage data relate to weight.

EXAMPLE 1

Preparation of Procollagen Peptide (Type III)

Procollagen peptide (type III) is prepared by the action of collagenase on procollagen (type III) at 37° C. The peptide is not exposed to any denaturing agents during this time. A modified process is used to prepare larger amounts of the peptide. All steps in the process up to the exposure to collagenase are carried out in a cold room. The various NaCl solutions used for solubilization contain 0.05M Tris-HCl, pH 7.4, 0.01M EDTA, sodium azide (200 mg/ml) and the protease inhibitors phenylmethylsulfonyl fluoride (3 µg/ml) and p-chloromercuribenzoate (3 µg/ml).

Fetal calf skin (3 kg) is homogenized and extracted for two days in 10 l of 1M NaCl. Dissolved collagen is precipitated from the extraction solution by addition of solid NaCl to a final concentration of 2.5M. After the precipitate has been stirred overnight, the precipitate is collected by centrifugation (1800×g, 20 minutes), washed twice with 2.5M NaCl and redissolved by stirring it overnight in 10 l of 0.5M NaCl. Small amounts of insoluble material are removed by centrifugation. The mixture of collagen (type III) and procollagen (type III) obtained in this way is precipitated with 1.6M NaCl. The precipitate is then suspended in 2 l of 0.05M Tris-HCl (pH 8.0) and after addition of 0.02M $CaCl_2$, the mixture is heated at 50° C. for 20 minutes and then incubated with 1500 U of bacterial collagenase (CLSPA, Worthington, USA) per gram of wet precipitate at 37° C. for 3 hours. After the exposure to collagenase, the precipitate which is formed is removed by centrifugation, and the solution is dialyzed against 0.005M Tris-HCl, pH 8, 6.8M urea and passed through a DEAE-cellulose column (5.0×30 cm) which has been equilibrated with the same buffer.

The proteins bound to the column are washed out with NaCl solutions with the concentration thereof rising from 0 to 0.3M. The total amount eluted is 2 l. The solution flowing out of the column is examined for absorption at 236 nm and for its antigen activity by use of antibodies which are specific for the amino-terminal segment of procollagen (type III). It is normally the last peak eluted from the column which contains the procollagen peptide (type III). Salts are removed from the peptide by dialysis against distilled water, and the peptide is freeze-dried (lyophilized). Subsequent purification is carried out on a column of agarose A 1.5M (2×120 cm) (from Biorad) which is equilibrated with 1M $CaCl_2$, 0.05M Tris-HCl, pH 7.5.

EXAMPLE 2

Hybridoma Preparation

Mice of the SJL strain are immunized intramuscularly with 5 µg of procollagen peptide (type III), obtained as in Example 1, in the presence of complete Freund's adjuvant. The immune response is enhanced after four weeks and after three months by another intramuscular injection of 5 µg of procollagen peptide (type III) in the presence of incomplete Freund's adjuvant. Three days before the fusion, the immune response is boosted by intraperitoneal injection of a further 50 µg of procollagen peptide (type III).

For the fusion, the animals are sacrificed, and the spleen cells are isolated. The spleen cells are fused with the myeloma cell line P3X63AG8.653 in the presence of polyethylene glycol. Spleen cell×P3X363AG8.653 hybrids are selected by cultivation of the fusion mixture in hypoxanthine/aminopterin/thymidine medium for a period of two weeks to select for spleen cell×P3X363AG8.653 hybrids. The resulting cell clones are subcloned several times to obtain a monoclonal cell line. The supernatants of the resulting cell colonies clones are assayed for antibody production in a radioimmunological binding assay. The monoclonal antibody P III P 226 is obtained in this way. The resulting cell line is deposited at the ECACC under the number 88030202.

Another resulting cell line, from which the monoclonal antibody P III P 296 is obtained, is deposited at the ECACC under the number 87042308.

EXAMPLE 3

Radioimmunological Binding Assay

300 µl of cell culture supernatant, or another sample such as, for example, ascites after cultivation of hybridoma cells in the abdominal cavity of mice, are incubated overnight with 100 µl of a $^{125}$I-procollagen peptide (type III) solution (1 ng of protein/100 µl, prepared as described in European Patent 4940, Example 1). The antigen-antibody complexes which are formed are precipitated by addition of anti-mouse IgG serum from sheep or another species. After centrifugation and decantation of the supernatant, the amount of precipitated radioactivity is determined in a γ-scintillation spectrometer.

EXAMPLE 4

Radioimmunoassay 0.2 ml of the sample which is to be analyzed, or of procollagen peptide (type III) standard, is incubated at 4° C. overnight with an amount of P III P 296 (in 0.1 ml of buffer) which is limiting with respect to the amount of labeled antigen, and 0.1 ml of $^{125}$I-labeled procollagen peptide (type III) (contains 1 ng of protein). The mixture is then incubated with a previously tested amount of anti-mouse IgG serum from sheep in the presence of 10% polyethylene glycol (PEG 6000) for 1 h. The precipitated antigen/antibody complexes are spun down (1500×g) and, after decantation, the radioactivity is determined in a γ-scintillation spectrometer.

Figure 1A:
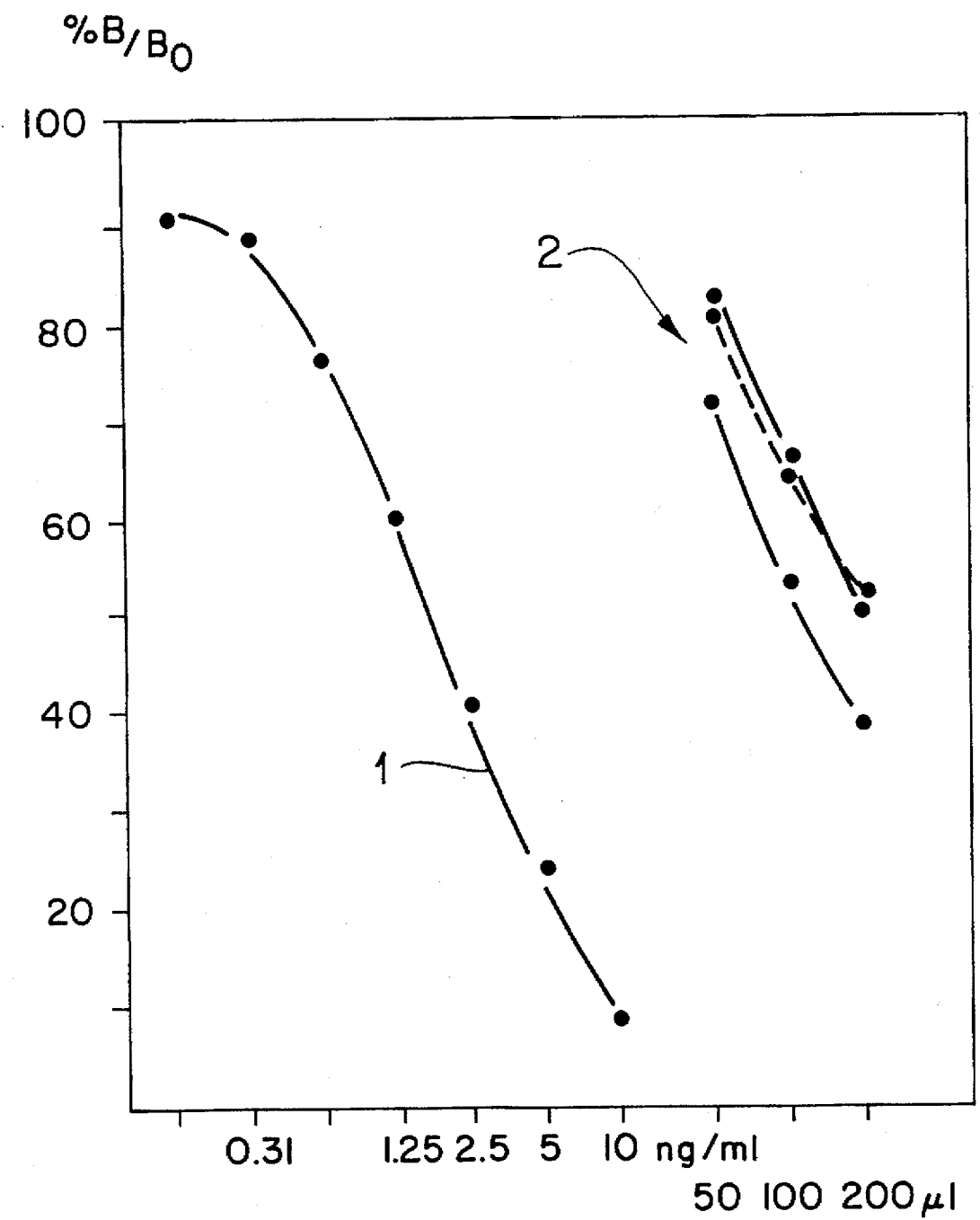
FIGS. 1(a) and (b). Calibration plot (1) and serum dilution plots (2) with P III P 296 (a) comparing with the method of European Patent 4940 and using monoclonal antibodies (b).
Figure 1B:
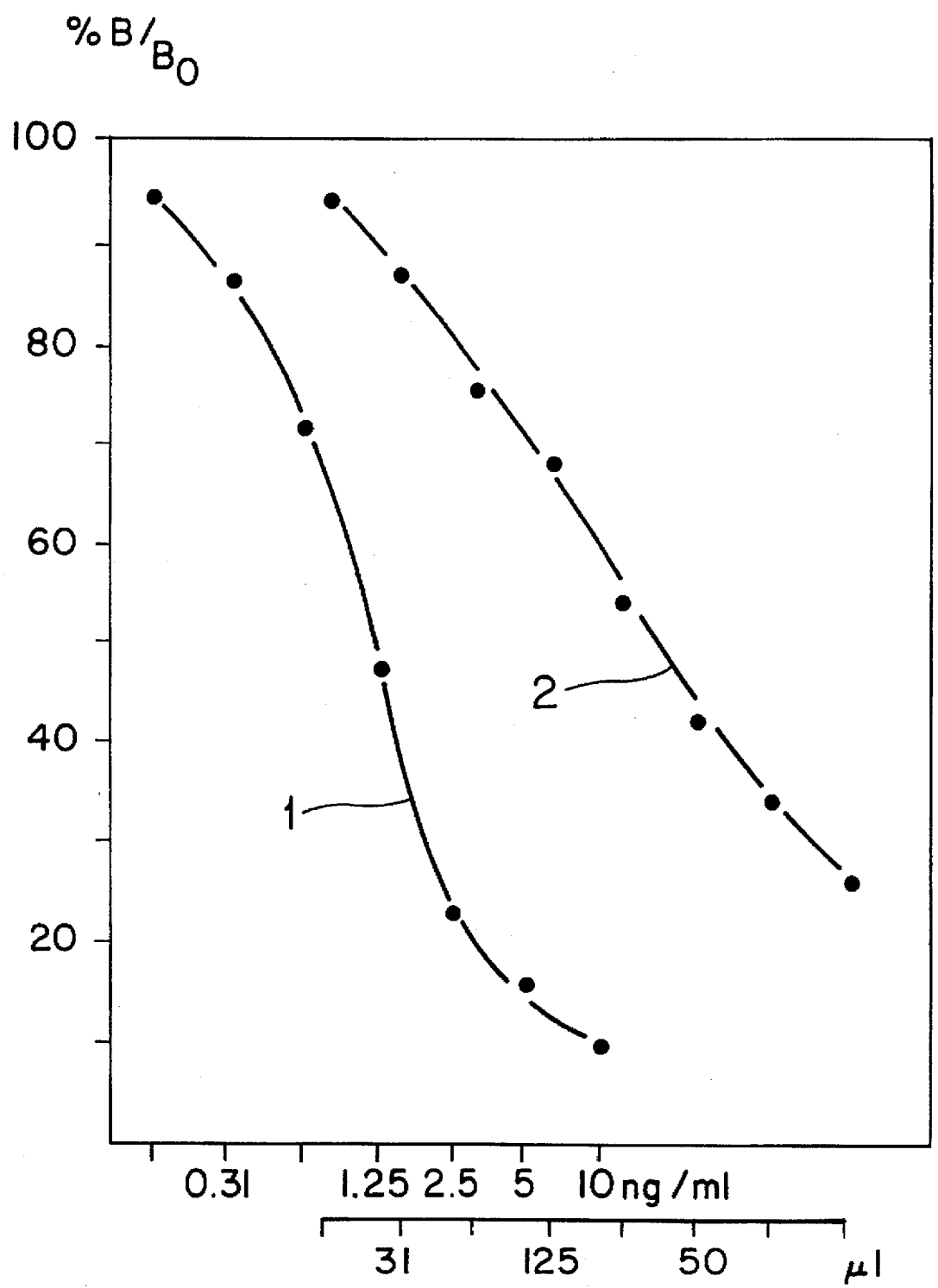

It is then possible, by comparison with a calibration plot which has been constructed by using standards with different amounts of procollagen peptide (type III), to determine the concentration of procollagen peptide (type III) in the unknown solution. FIG. 1 shows the calibration plot (1) and serum dilution plots (2) with P III P 296 (a) compared with the method of European Patent 4940 using polyclonal antibodies (b).

EXAMPLE 5

Radiolabeling of the Antibodies 0.2 ml of a solution containing 0.2 mg of monoclonal P III P 296 as described in german patent application P 3,714, 633.5, Example 2, or of another antibody in 0.05M phosphate buffer, pH 7.4, are placed in a polystyrene assay tube (12×55 mm), and 100 MBq of Na$^{125}$I solution, buffered with 10 µl of 0.5M phosphate buffer, pH 7.4, are added. Addition of 50 µl of an aqueous solution of 20 µg of chloramine T is followed by mixing for 1 min. The iodination reaction is then stopped by addition of 50 µl of an aqueous solution of 20 µg of sodium disulfite.

The unreacted Na$^{125}$I is then removed from the $^{125}$I-labeled P III P 296 or other antibody by chromatography on an anion exchanger. The chromatographic fractions which contain the purified $^{125}$I-labeled antibody are diluted with a solution of 20 g of Tween 20 and 14.6 of $Na_2$EDTA in one liter of 0.05M tris-HCl buffer, pH 8.0, so that the concentration of the labeled antibody is 200 µg/l.

EXAMPLE 6

Coating of Assay Tubes with the Antibodies

To immobilize antibodies on polystyrene assay tubes (12×75 mm) 300 µl of a solution of 4 mg/l antibody, for example P III P 226 or P III P 296, in 0.01M sodium phosphate buffer, pH 6.4, is placed in each tube and incubated at room temperature overnight. The antibody solution is then removed by aspiration, and 500 µl of a 1% strength solution of bovine serum albumin in 0.05M Tris-citrate, pH 7.5, are placed in each tube. After incubation at room temperature overnight the solution is removed by aspiration. The antibody-coated tubes are dried over silica gel.

EXAMPLE 7

Immunoradiometric Assay (Radioimmunometric Assay, IRMA)

0.1 ml of the sample which is to be analyzed, or 0.1 ml of procollagen (type III) standard, is incubated in polystyrene assay tubes which have previously been coated with 1.2 µg of the monoclonal P III P 296, with the addition of 0.1 ml of phosphate-buffered saline (PBS), at room temperature for 2 hours. The assay tubes are then washed twice with 1 ml of PBS, with decantation, each time. Then 200 µl of $^{125}$I-labeled monoclonal P III P antibodies (contains 40 ng of antibodies) are placed in the tubes and incubated at room temperature for 2 hours. The antibody/antigen/$^{125}$I-antibody complexes bound to the assay tube wall are washed twice with 1 ml of PBS, followed by decantation, each time, and their radioactivity is determined in a scintillation counter.

Figure 2:
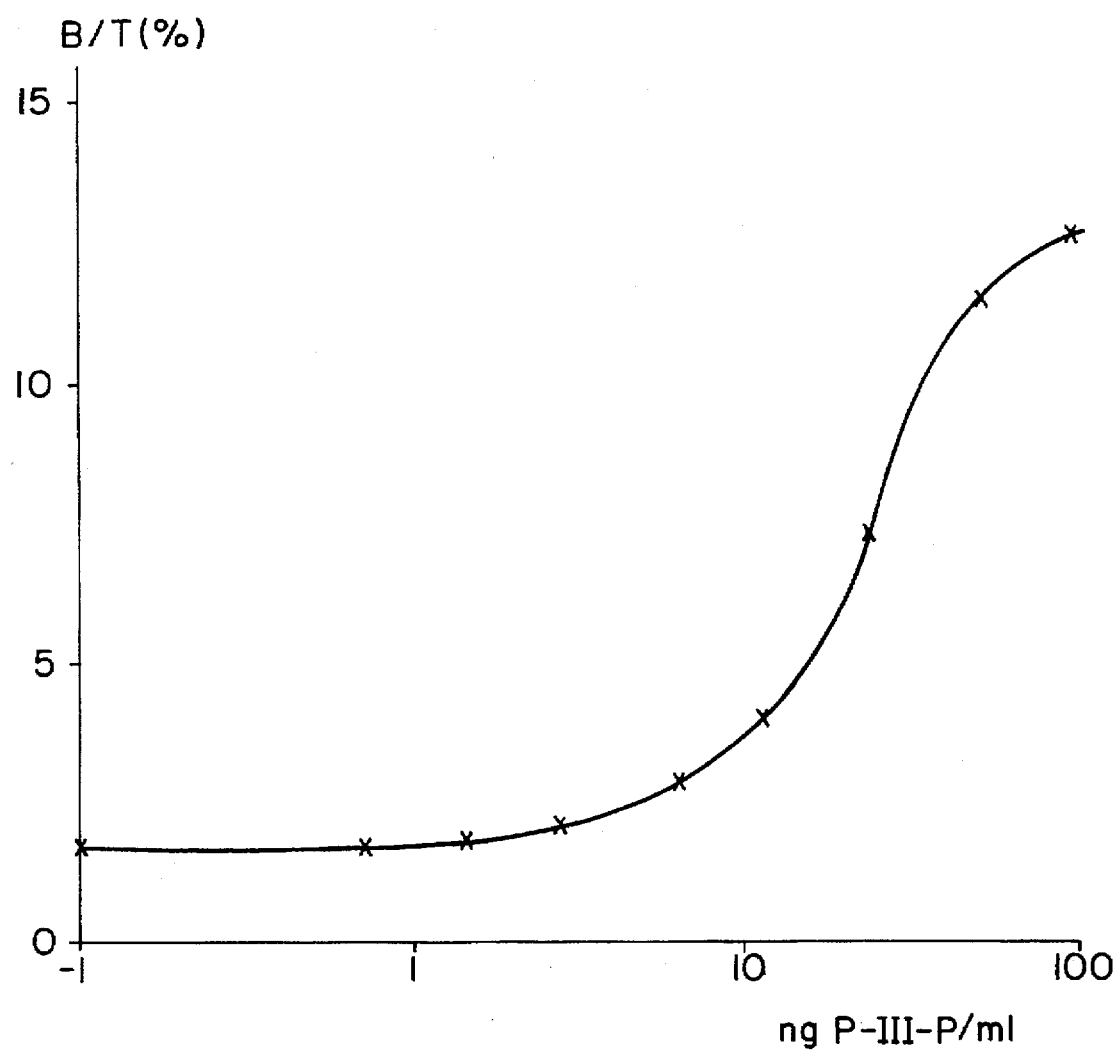
FIG. 2. Calibration plot of the radioimmunometric assay of Example 8. B/T denotes: bound/total antibody.

It is then possible, by comparison with a calibration plot which has been constructed by using standards with different amounts of procollagen peptide (type III), to calculate the concentration of procollagen peptide (type III) in the unknown sample solution. FIG. 2 shows the calibration plot of the radioimmunometric assay. (B/T denotes: bound/total antibody).

EXAMPLE 8

Immunoradiometric Assay 0.1 ml of the sample for analysis, or of procollagen peptide (type III) standard, is incubated in polystyrene assay tubes which have been coated with the monoclonal antibody P III P 226 as in Example 6, with the addition of 0.1 ml of phosphate-buffered saline (PBS) at room temperature for 2 hours. The assay tubes are subsequently washed twice with 1 ml of PBS each time. Then 200 µl of $^{125}$I-labeled antibody P III P 296 (=40 ng of antibody), or of another antibody, are placed in the tubes and incubated at room temperature for 2 hours. The radioactivity of the antibody-antigen-$^{125}$I-antibody complexes bound to the tube wall is determined, after two washings with 1 ml of PBS each time and subsequent decantation, in a gamma scintillation spectrometer.

Figure 4:
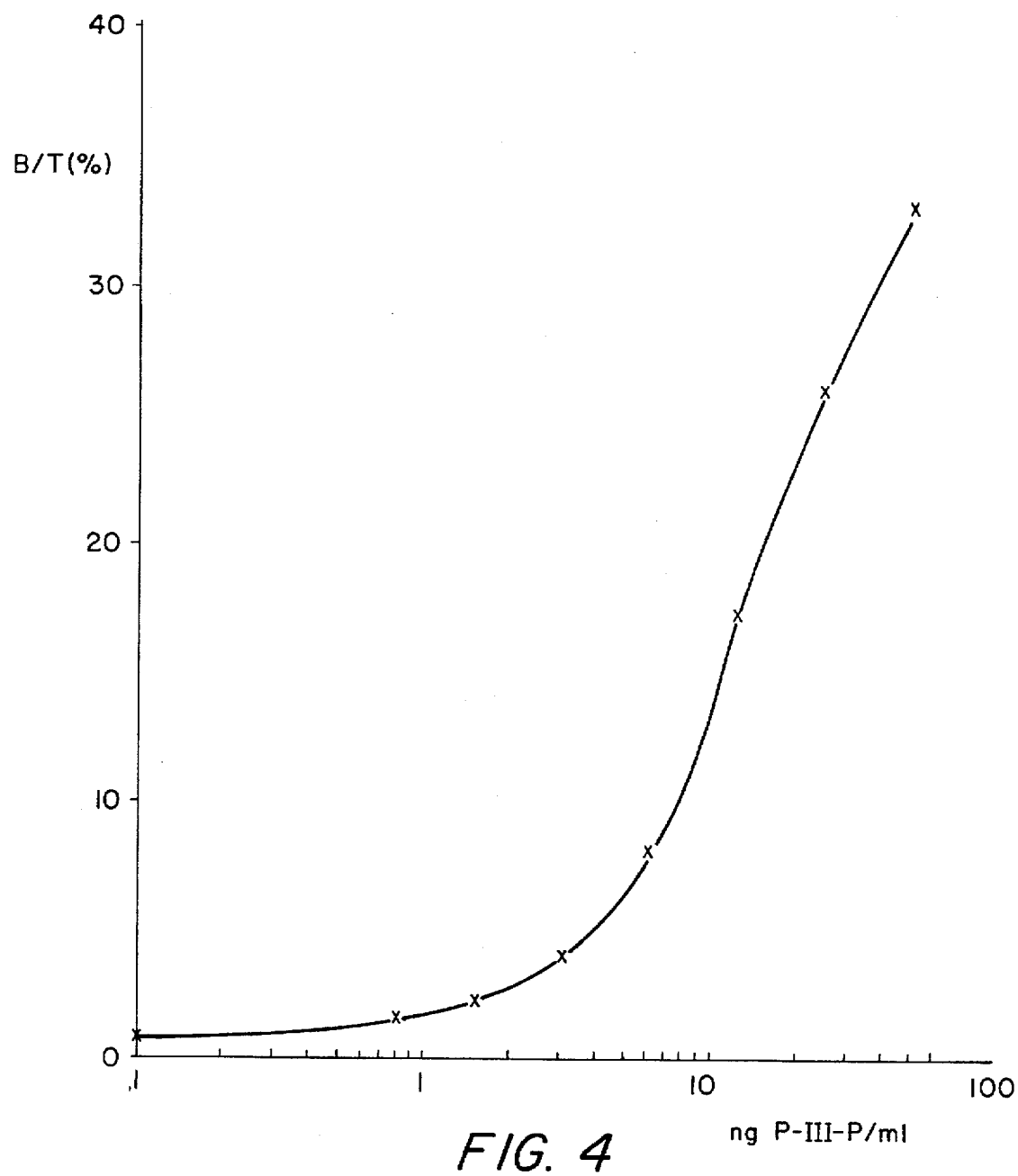
FIG. 4. Calibration plot for of the radioimmunometric assay for Example 9. B/T denotes: bound/total antibody.

It is then possible to calculate the concentration of procollagen peptide (type III) in the unknown sample solution by comparison with a calibration plot which has been constructed by employing standards containing different amounts of procollagen peptide (type III). FIG. 4 shows the calibration plot of the immunoradiometric assay (B/T denotes the ratio of bound to total radioactivity employed).

EXAMPLE 9

Determination of the Molecular Weight Distribution of the Antigens which React with P III P 296 and are Present in Human Serum 1 ml of serum is fractionated by gel filtration chromatography on an allyldextran crosslinked with N,N'-methylenebisacrylamide [®Sephacryl S 300 column (1.6× 130 cm)] equilibrated in phosphate-buffered saline (PBS) containing 0.04% of a nonionic detergent, for example a polyoxyethylene sorbitan monolaurate (Tween 20) in 3.3 ml fractions. 0.2 ml of each of the fractions is used in the radioimmunoassay described in Example 4. FIG. 3 shows the elution profile of the antigen determined using P III P 296, comparing with the profile of the antigen determined using the polyclonal antibodies:

Peak 4/4a corresponds to pN collagen and intact amino-terminal procollagen (type III)
Peak 5/5a corresponds to amino-terminal procollagen peptide (type III)=(P III P)
Peak 6/6a corresponds to Col 1 and breakdown products of amino-terminal procollagen peptide (type III) with the same molecular weight as Col 1.

The concentration of the substances in the relevant fractions can be determined using a procollagen peptide (type III) calibration plot.

EXAMPLE 10

Determination of the Molecular Weight Distribution of the Antigens in Human Serum which React with P III P 226

1 ml of serum is fractionated by gel filtration chromatography on allyldextran crosslinked with N,N'-methylenebisacrylamide [®Sephacryl S 300 column (1.6× 130 cm)], equilibrated in PBS containing 0.04% of a nonionic detergent, for example a polyethoxylated sorbitan monolaurate (Tween 20). 0.2 ml of each individual fraction is incubated with the antibody to be investigated, in an amount which is limiting with regard to the amount of labeled antigen (in 0.1 ml of buffer), and with 0.1 ml of $^{125}$I-labeled procollagen peptide (type III) (contains 1 of protein) at 4° C. overnight. It is subsequently incubated with a previously assayed amount of anti-mouse IgG serum from sheep in the presence of 10% polyethylene glycol (PEG 6000) for 1 hour. The precipitated antigen-antibody complexes are spun down (1500×g) and, after decantation, the radioactivity is determined in a gamma scintillation spectrometer. It is then possible to determine, by comparison with a calibration plot which has been constructed by employing standards containing different amounts of procollagen peptide (type III), the concentration in the chromatography fractions of antigen which react with the antibody employed. FIG. 5 shows the elution profile of the antigen determined using P III P 226 by comparison with the profile of the antigen determined with the aid of polyclonal antibodies.

We claim:

1. The monoclonal antibody P III P 226 of the hybridoma cell line ECACC 88030202.

2. A diagnostic composition for determining the amount of type III procollagen peptide in body fluids, which comprises an effective amount of the monoclonal antibody as claimed in claim 1, mixed with a diagnostically acceptable vehicle.

3. A hybridoma cell line which produces an antibody which binds to the same epitope as the antibody claimed in claim 1 and is formed by fusion of cells from a myeloma cell line and of lymphocytes from an animal which has previously been immunized with type III procollagen peptide.

4. A method for the quantitative immunological determination of type III procollagen peptide or of the type III procollagen using antibodies, which comprises
    a) reacting a liquid sample which contains amino-terminal type III procollagen peptide or type III procollagen with a monoclonal antibody as claimed in claim 1; and
    b) determining the amount of amino-terminal type III procollagen peptide or of the type III procollagen via the antigen-antibody complex formed.

5. The monoclonal antibody P III P 296 of the hybridoma cell line ECACC 87042308.

6. A diagnostic composition for determining the amount of type III procollagen peptide in body fluids, which comprises an effective amount of the monoclonal antibody as claimed in claim 5, mixed with a diagnostically acceptable vehicle.

7. A hybridoma cell line which produces an antibody which binds to the same epitope as the antibody claimed in claim 5 and is formed by fusion of cells from a myeloma cell line and of lymphocytes from an animal which has previously been immunized with type III procollagen peptide.

8. A method for the quantitative immunological determination of type III procollagen peptide or of the type III procollagen using antibodies, which comprises a) reacting a liquid sample which contains amino-terminal type III procollagen peptide or type III procollagen with a monoclonal antibody as claimed in claim 5; and b) determining the amount of amino-terminal type III procollagen peptide or of the type III procollagen via the antigen-antibody complex formed.

9. The hybridoma cell line ECACC 88030202.

10. The hybridoma cell line ECACC 87042308.

11. A method for producing a monoclonal antibody comprising obtaining the hybridoma cell line ECACC 87042308 or ECACC 88030202 and isolating a monoclonal antibody produced therefrom.

12. The method as claimed in claim 11, wherein the hybridoma cell line is ECACC 87042308.

13. The method as claimed in claim 11, wherein the hybridoma cell line is ECACC 88030202.

14. A process for the preparation of a monoclonal antibody against amino terminal type III procollagen peptide which comprises:

a) immunizing animals with amino-terminal type III procollagen peptide;

b) obtaining lymphocytes and fusing said lymphocytes with myeloma cells;

c) selecting the hybrids for the presence of an antibody which specifically binds an epitope of amino-terminal type III procollagen peptide, said epitope not being present in Col 1;

d) cloning a hybridoma, wherein the hybridoma cell line ECACC 88030202 is employed; and e) isolating the antibodies from cloned hybridoma.

15. A process for the preparation of a monoclonal antibody against amino terminal type III procollagen peptide which comprises:

a) immunizing animals with amino-terminal type III procollagen peptide;

b) obtaining lymphocytes and fusing said lymphocytes with myeloma cells;

c) selecting the hybrids for the presence of an antibody which specifically binds an epitope of amino-terminal type III procollagen peptide, said epitope not being present in Col 1;

d) cloning a hybridoma, wherein the hybridoma cell line ECACC 87042308 is employed; and e) isolating the antibodies from the cloned hybridoma.

16. A method for the quantitative immunological determination of type III procollagen peptide or of the type III procollagen using antibodies, which comprises:

a) coupling the monoclonal antibody which specifically binds an epitope of amino-terminal type III procollagen peptide, said epitope not being present in Col 1, to a solid matrix;

b) reacting a liquid sample which contains amino-terminal type III procollagen peptide or type III procollagen with said antibody; and c) detecting the bound antigen using a labeled antibody P III P 226 of the hybridoma cell line ECACC 88030202.

17. A method for the quantitative immunological determination of type III procollagen peptide or of the type III procollagen using antibodies, which comprises:

a) coupling the monoclonal antibody which specifically binds an epitope of amino-terminal type III procollagen peptide, said epitope not being present in Col 1, to a solid matrix;

b) reacting a liquid sample which contains amino-terminal type III procollagen peptide or type III procollagen with said antibody; and c) detecting the bound antigen using a labeled antibody P III P 296 of the hybridoma cell line ECACC 87042308.

18. A method for the quantitative immunological determination of type III procollagen peptide or of the type III procollagen using antibodies, which comprises:

a) coupling the antibody P III P 226 of the hybridoma cell line ECACC 88030202 to a solid matrix;

b) reacting a liquid sample which contains amino-terminal type III procollagen peptide or type III procollagen with said antibody; and c) detecting the bound antigen by labeled monoclonal or polyclonal antibodies with specificity for type III procollagen peptide or type III procollagen.

19. A method for the quantitative immunological determination of type III procollagen peptide or of the type III procollagen using antibodies, which comprises:

a) coupling the antibody P III P 296 of the hybridoma cell line ECACC 87042308 to a solid matrix;

b) reacting a liquid sample which contains amino-terminal type III procollagen peptide or type III procollagen with said antibody; and c) detecting the bound antigen by labeled monoclonal or polyclonal antibodies with specificity for type III procollagen peptide or type III procollagen.

20. A method for the quantitative immunological determination of type III procollagen peptide or of the type III procollagen using antibodies, which comprises:

a) coupling an antibody P III P 226 of the hybridoma cell line ECACC 88030202 to a solid matrix;

b) reacting a liquid sample which contains amino-terminal type III procollagen peptide or type III procollagen with said antibody; and c) detecting the bound antigen by a labeled monoclonal antibody which specifically binds an epitope of amino-terminal type III procollagen peptide, said epitope not being present in Col 1.

21. The method as claimed in claim 20, wherein the labeled antibody employed in step c) is P III P 296 of the hybridoma cell line ECACC 87042308.

22. A method for the quantitative immunological determination of type III procollagen peptide or of the type III procollagen using antibodies, which comprises:

a) coupling an antibody P III P 296 of the hybridoma cell line ECACC 87042308 to a solid matrix;

b) reacting a liquid sample which contains amino-terminal type III procollagen peptide or type III procollagen with said antibody; and c) detecting the bound antigen by a labeled monoclonal antibody which specifically binds an epitope of amino-terminal type III procollagen peptide, said epitope not being present in Col 1.

23. The method as claimed in claim 22, wherein the labeled antibody employed in step c) is P III P 226 of the hybridoma cell line ECACC 88030202.

24. A method for the quantitative immunological determination of type III procollagen peptide or of the type III procollagen using antibodies, which comprises:

a) coupling a polyclonal or monoclonal antibody with specificity for type III procollagen peptide and/or type III procollagen to a solid matrix;

b) reacting a liquid sample which contains amino-terminal type III procollagen peptide or type III procollagen with said antibody; and c) detecting the bound antigen using a labeled antibody P III P 226 of the hybridoma cell line ECACC 88030202.

25. A method for the quantitative immunological determination of type III procollagen peptide or of the type III procollagen using antibodies, which comprises:

a) coupling a polyclonal or monoclonal antibody with specificity for type III procollagen peptide and/or type III procollagen to a solid matrix;

b) reacting a liquid sample which contains amino-terminal type III procollagen peptide or type III procollagen with said antibody; and c) detecting the bound antigen using a labeled antibody P III P 296 of the hybridoma cell line ECACC 87042308.

* * * * *